Young et al.

[45] Date of Patent: Apr. 28, 1987

[54] 2-[(SUBSTITUTED)-PHENOXYMETHYL]-QUINOLINES

[75] Inventors: Robert N. Young, Quebec; Robert Zamboni, Longueuil, both of Canada

[73] Assignee: Merck Frosst Canada, Inc., Kirkland, Canada

[21] Appl. No.: 746,205

[22] Filed: Jun. 18, 1985

[51] Int. Cl.$^4$ ..................... A61K 31/47; C07D 215/14
[52] U.S. Cl. ................................. 514/311; 514/312; 514/313; 546/152; 546/153; 546/155; 546/156; 546/159
[58] Field of Search ..................... 514/311, 312, 313; 546/152, 153, 155, 156, 159

[56] References Cited

U.S. PATENT DOCUMENTS

| | | |
|---|---|---|
| 2727387 | 12/1977 | DEX . |
| 4,236,912 | 12/1980 | Johnston .............................. 546/157 |
| 4,408,076 | 10/1983 | Lee ....................................... 546/157 |
| 4,444,584 | 4/1984 | Serban ................................ 546/153 |

FOREIGN PATENT DOCUMENTS 1001405  6/1984  European Pat. Off. .

OTHER PUBLICATIONS

J. Chem. Soc. Dalton 1259, 1264 (1980), Antony Deeming et al.
Org. Reactions, VII, R. Adams, ed., p. 82, (1953).
Aldrich Fine Chemicals, 58, 145 (1986).
Reagents for Org. Syn., 4, Fieser & Fieser, 448-449 (1974).

Primary Examiner—Sam Rosen
Assistant Examiner—Robert Benson
Attorney, Agent, or Firm—Gabriel Lopez; Hesna J. Pfeiffer

[57] ABSTRACT

Compounds having the formula:

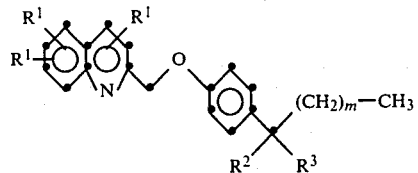

are selective antagonists of leukotrienes of $D_4$ and inhibitors of the syntheses of $LTA_4$, $B_4$, $C_4$, $D_4$, $E_4$, and $F_4$. These compounds are useful as anti-asthmatic, anti-allergic, anti-inflammatory agents, and cytoprotective agents.

7 Claims, No Drawings

2-[(SUBSTITUTED)-PHENOXYMETHYL]QUINOLINES

BACKGROUND OF THE INVENTION

This invention is directed to compounds which act as antagonists of the leukotrienes and inhibitors of the syntheses of $LTA_4$, $B_4$, $C_4$, $D_4$, $E_4$, and $F_4$.

The leukotrienes and their biological activities, especially their roles in various disease states and conditions have been described. For example, see EP No. 140,684 (May 8, 1985), which is incorporated herein by reference.

Several classes of compounds exhibit ability to antagonize the action of leukotrienes in mammals, especially humans. See for example: United Kingdom Patent Specification Nos. 2,058,785 and 2,094,301; and European Patent Application Nos. 56,172, 61,800 and 68,739.

EP No. 110,405 (June 13, 1984) describes anti-inflammatory and antiallergic substituted benzenes which are disclosed to be leukotriene inhibitors, i.e., inhibitors of the 5-lipoxygenase pathway.

SUMMARY OF THE INVENTION

It has now been found that the 4-substituted phenoxyquinoline compounds of the present invention exhibit surprisingly and unexpectedly enhanced biological activity as leukotriene synthesis inhibitors and antagonists of their action when compared to positional isomers thereof, such as 3-substituted phenoxyquinoline of EP No. 110,405.

The present invention relates to compounds having activity as leukotriene and SRS-A antagonists or inhibitors, to methods for their preparation, to intermediates useful in their preparation and to methods and pharmaceutical formulations for using these compounds in mammals (especially humans).

Because of their activity as leukotriene antagonists and inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

DETAILED DESCRIPTION

The compounds of this invention are best realized by Formula I:

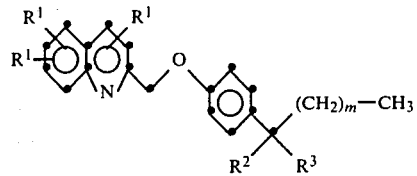

wherein:

$R^1$ is H, halogen, $C_1$-$C_6$ alkyl, $C_2$-$C_6$ alkenyl, $C_2$-$C_6$ alkynyl, —$CF_3$, —$OR^2$, —$SR^2$, —$NR^2R^2$, —CHO, —$COOR^2$, —(C=O)$R^2$, —C(OH)$R^2R^2$, —CN, —$NO_2$, substituted or unsubstituted phenyl, substituted or unsubstituted benzyl, or substituted or unsubstituted phenethyl;

$R^2$ is H, $C_1$-$C_6$ alkyl, $C_2$-$C_6$ alkenyl, $C_2$-$C_6$ alkynyl, —$CF_3$, substituted or unsubstituted phenyl, substituted or unsubstituted benzyl, or substituted or unsubstituted phenethyl;

$R^3$ is —$OR^4$, —$SR^4$, or —$NR^4R^4$;

$R^4$ is H, or $C_1$-$C_6$ alkyl, —(C=O)$R^2$, unsubstituted phenyl, or unsubstituted benzyl;

m is 1-6; and the pharmaceutically acceptable salts thereof.

Alkyl, alkenyl, and alkynyl are intended to include linear, branched, and cyclic structures. Thus, alkyl would include n-butyl, sec-butyl, tert-butyl, cyclobutyl, etc.

Substituted phenyl, benzyl, and phenethyl include 1-2 substituents selected from $C_1$-$C_6$alkyl, —$R^3$, —$NO_2$, $SCF_3$, halogen, —$COR^3$, —CN, or —$CF_3$.

Halogen includes F, Cl, Br and I.

It is intended that the definitions of any substituent (e.g., $R^1$, $R^2$, m, etc.) in a particular molecule is independent of its definitions elsewhere in the molecule. Thus, —$NR^4R^4$ represents —NHH, —$NHCH_3$, —N($CH_3$)($C_2H_5$), etc.

Preferred compounds of Formula I are those wherein $R^2$ is H, $R^3$ is OH, and m is 4.

The compounds of Formula I are active as antagonists of SRS-A and especially of leukotrienes $D_4$. These compounds also have inhibitory activity on leukotriene biosynthesis. The activity of the compounds of Formula I can be detected and evaluated by methods known in the art. See for example, Kadin, U.S. Pat. No. 4,296,129.

The ability of the compounds of Formula I to antagonize the effects of the leukotrienes and to inhibit the biosynthesis of leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. It will be understood that in this paragraph and in the discussion of methods of treatment which follows, references to the compounds of Formula I are meant to include the pharmaceutically acceptable salts.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP No. 140,684.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.01 mg to about 100 mg per kg body weight of a mammal, preferably 0.1 mg to about 20 mg per kg, and most preferably 1 to 20 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

The effective daily dosage level for compounds of Formula I inducing cytoprotection in mammals, especially humans, will generally range from about 0.1 mg/kg to about 100 mg/kg, preferably from about 1 mg/kg to about 100 mg/kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic acids including inorganic acids and organic acids.

When the compound of the present invention is basic, salts may be prepared from pharmaceutically acceptable non-toxic acids, including inorganic and organic acids, such acids include acetic, benzensulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, panoic, pantothenic, phosphoric, succinic, sulfuric, tataric acid, p-toluenesulfonic and the like. Particularly preferred are hydrobromic, hydrochloric, phosphoric and sulfuric acids.

The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.01 mg to about 10 mg (preferably from about 0.1 mg to about 10 mg) of a compound of Formula I per kg of body weight per day and for cytoprotective use from about 0.1 mg to about 20 mg (preferably from about 1 mg to about 20 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 100 mg per kg and for cytoprotective use from about 0.1 mg to about 100 mg (preferably from about 1 mg to about 100 mg and more preferably from about 10 mg to about 100 mg) of a compound of Formula I per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the compounds of Formula I may also be administered by controlled release means and/or delivery devices such as those described in U.S. Pat. Nos.

3,845,770; 3,916,899; 3,536,809; 3,598,123; 3,630,200 and 4,008,719, the disclosures of which are hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the compounds of Formula I:

| Injectable Suspension | mg/ml |
|---|---|
| Compound of Formula I | 2.0 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Tablet | mg/tablet |
|---|---|
| Compound of Formula I | 25.0 |
| Microcrystalline Cellulose | 325.0 |
| Providone | 14.0 |
| Microcrystalline Cellulose | 90.0 |
| Pregelatinized Starch | 43.5 |
| Magnesium Stearate | 2-2.5 |
| | 500 |

| Capsule | mg/capsule |
|---|---|
| Compound of Formula I | 25.0 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000. Combinations of a compound of the Formula I and other active ingredients will generally also be within the aforementioned range, but in each case, an effective dose of each active ingredient should be used.

NSAIDs can be characterized into five groups:

(1) the propionic acid derivatives;

(2) the acetic acid derivatives;

(3) the fenamic acid derivatives;

(4) the biphenylcarboxylic acid derivatives; and (5) the oxicams or a pharmaceutically acceptable salt thereof. NSAIDs which are within the scope of this invention are those disclosed in EP No. 140,684.

Pharmaceutical compositions comprising the Formula I compounds may also contain inhibitors of the biosynthesis of the leukotrienes such as are disclosed in EP No. 138,481 (Apr. 24, 1985), EP No. 115,394 (Aug. 8, 1984), EP No. 136,893 (Apr. 10, 1985), and EP No. 140,709 (May 5, 1985), which are hereby incorporated herein by reference.

The compounds of the Formula I may also be used in combination with leukotriene antagonists such as those disclosed in EP No. 106,565 (Apr. 25, 1984) and EP No. 104,885 (Apr. 4, 1984) which are hereby incorporated herein by reference and others known in the art such as those disclosed in European Patent Application Nos. 56,172 (July 21, 1982) and 61,800 (Oct. 6, 1982); and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP No. 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

Compounds of the present invention can be prepared according to the methods taught in EP No. 110,405 or according to the following scheme.

SCHEME I

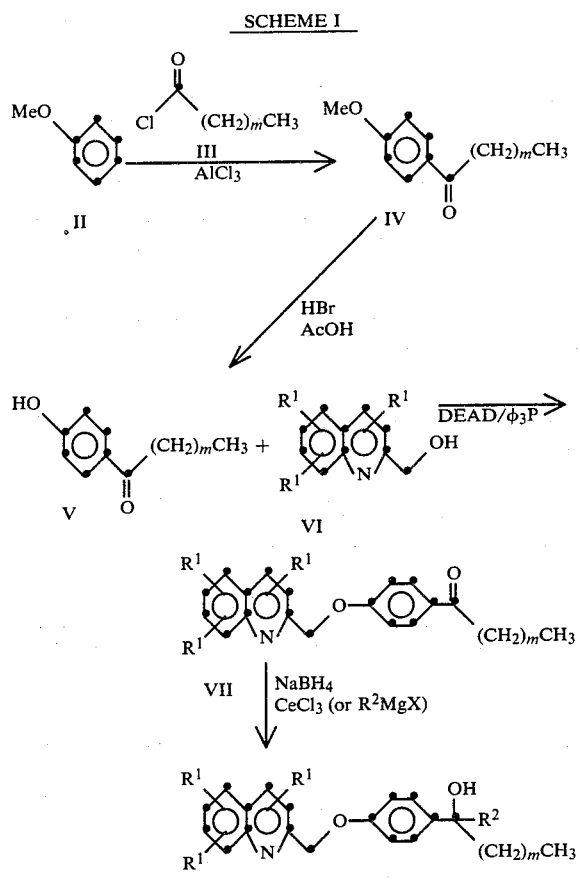

SCHEME II

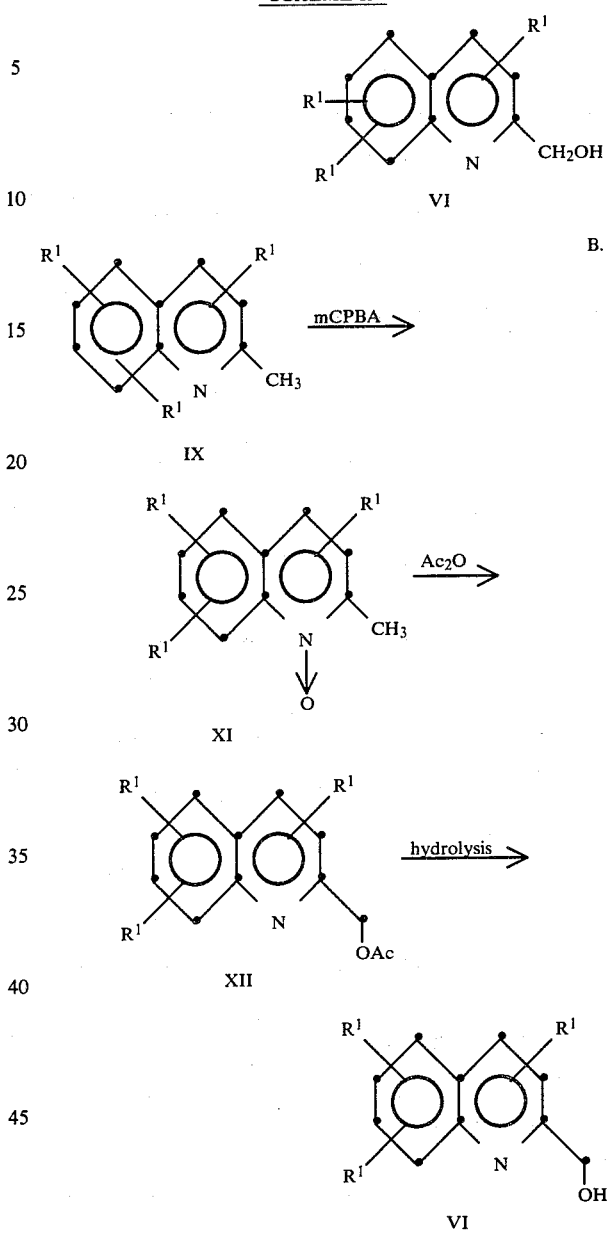

Referring to Scheme I, anisole II is condensed with an acid chloride of formula III using a suitable condensation reagent such as AlCl$_3$ to provide ketone of Structure IV. The methyl ether in IV is removed with a strong acid such as HBr to provide phenol V. Phenol V is coupled with quinoline of Structure VI using a suitable condensation catalyst such as diethylazodicarboxylate/$\phi_3$P to provide VII. In cases where $R^1$, is to provide carbonyl groups they are used in their protected forms. The ketone in Structure VII is reduced using a reducing agent such as sodium borohydride (or, alternatively, VII may be reacted with an organometalic reagent such as $R^2$MgBr) to provide quinoline derivatives I. In cases where $R^1$ and $R_2$ contain carbonyl groups in a protected form they are regenerated at this stage to provide I. The hydroxyl group in VIII is transformed to $OR^4$, $—SR^4$, or $—NR^4R^4$ using standard techniques.

Referring to Scheme II, an aniline of general structure VIII is reacted with crotonaldehyde and strong acid such as hydrochloric acid (6N) to provide the quinaldine of general structure IX.

IX is oxidized (A) with a strong oxidant such as potassium permanganate in a polar solvent such as aqueous, t-butanol to provide the acid of general formula X. Reduction of X with a reducing agent such as lithium aluminum hydride in an inert solvent such as diethyl ether provides the alcohols of general structure VI.

Alternatively (B), the quinaldines IX can be oxidized with an oxidizing agent such as hydrogen peroxide or m-chloroperbenzoic acid to provide the N-oxide of general formula XI. Reaction of XI with acetic anhydride provides the acetate of general structure XII. Hydrolysis of the acetate with aqueous base such as sodium hydroxide in a solubilizing cosolvent such as tetrahydrofuran or methanol provides the alcohols of general formula VI.

The following examples further define the invention and are provided as illustrative and not as limiting.

Temperatures are in degrees Celsius.

EXAMPLE 1

2-[4-(1-Hydroxyhexyl)phenoxymethyl)]quinoline

Step 1: Preparation of 1-(4-methoxyphenyl)hexanone

To a solution of anisole (22 g) in dichloro methane (11) and hexanoyl chloride (33 g) at $-20°$ was added portionwise over 30 minutes aluminum chloride (32 g). The reaction was stirred 2 hours at $-20°$ and then quenched with ice and 11 1N HCl. The organic layer was separated, dried ($Na_2SO_4$), and evaporated. Chromatography of the residue using 5% ethylacetate in hexane afforded 20 g of the title compound: m.p.=32°-35°.

p.m.r. ($CDCl_3$) 0.9(m,3H), 1.4(m,4H), 1.7(m,2H), 2.8(t,2H), 3.8(t,3H), 6.9(d,2H), 7.9 p.p.m. (d,2H).

Step 2: Preparation of 1-(4-hydroxyphenyl)-hexanone

A solution of 1-(4-methoxyphenyl)hexanone (5 g) in acetic acid (50 ml) and 48% HBr was heated overnight at 120°. The reaction mixture was poured onto ice and extracted with ethylacetate (500 ml). The ethyl acetate layer was washed with $NaHCO_3$ (200 ml), dried, and evaporated. Chromatography of the residue using 30% ethylacetate in hexane afforded 1.7 g of the title compound.

p.m.r. ($CDCl_3$) 0.9(m,3H), 1.4(m,4H), 1.8(m,2H), 2.95(t,3H), 6.2-7.0(bs,1H), 6.9(d,2H) and 7.9 p.p.m. (d,2H).

Step 3: Preparation of 2-[4-(1-oxohexyl)phenoxymethyl)quinoline

To a solution of quinolinylmethanol (1.1 g), triphenylphosphine (1.8 g), and the hexanone of Step 2 above (1.3 g) at 0° in tetrahydrofuran was added dropwise diethylazodicarboxylate (1.1 ml) over 10 minutes. The reaction mixture was stirred 1 hour at room temperature and evaporated. Chromatography of the residue using 25% ethylacetate in hexane afforded the title compound 1.7 g: m.p.=78°-80°.

p.m.r. ($CDCl_3$) 0.9(3H), 1.4(m,4H), 1.8(m,2H), 2.9(t,3H), 5.35(s,2H), 7.1(d,2H), 7.5-8.2 p.p.m. (m,8H).

Step 4:

To a solution of the hexanone of Step 3 above (530 mg) in ethanol (20 ml) and tetrahydrofuran (3 ml) was added sodium borohydride (200 mg) and cerium chloride (20 mg). The reaction mixture was stirred at room temperature 4 hours and poured onto saturated $NH_4Cl$ and stirred 5 minutes at room temperature. Sodium hydroxide (50 ml of 1N) was added. The mixture was extracted with ethylacetate dried and evaporated. Recrystallization of the residue from hexane/ethylacetate afforded the title compound: m.p.=93°-94°.

Anal. for $C_{22}H_{25}NO_2$ Calc'd: C, 78.77; H, 7.52; N, 4.17. Found: C, 79.10; H, 7.85; N, 4.11.

EXAMPLE 2

COMPARATIVE ASSAY

The enhanced biological activity of the 4-substituted phenyl compound of the present invention can be demonstrated by comparison with their 3-substituted phenyl isomers. For example, 2-[4-(1-hydroxyhexylphenoxymethyl)]quinoline (see Example 1) was compared to its 3-(1-hydroxyhexylphenoxymethyl) analog in the PMN (leukotriene inhibitor) assay.

The data from this assay are shown in Table 2-1.

Rat Peritoneal Polymorphonuclear (PMN) Leukocyte Assay

Rats under ether anesthesia are injected (i.p.) with 8 ml of a suspension of sodium cascinate (6 grams in ca. 50 ml water). After 15-24 hr. the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted (350×g, 5 min.), resuspended in buffer with vigorous shaking, filtered, through lens paper, recentrifuged and finally suspended in buffer at a concentration of 10 cells/ml. A 500 µl aliquot of PMN suspension and test compound are preincubated for 2 minutes at 37° C., followed by the addition of 10 µM A-23187. The suspension is stirred for an additional 4 minutes then bioassayed for $LTD_4$ content by adding an aliquot to a second 500 µl portion of the PMN at 37° C. The $LTB_4$ produced in the first incubation causes aggregation of the second PMN, which is measured as a change in light transmission. The size of the assay aliquot is chosen to give a submaximal transmission change (usually $-70\%$) for the untreated control. The percentage inhibition of $LTB_4$ formation is calculated from the ratio of transmission change in the sample to the transmission change in the compound-free control.

TABLE 2-1

| COMPARISON OF ACTIVITY PMN ASSAY | | | | | | |
|---|---|---|---|---|---|---|
| | % Inhibition of $LTD_4$ Formation | | | | | |
| Compound | 5* | 1* | 0.2* | 0.04* | 0.008* | 0.0016* |
| Example 1 | 100 | 100 | 100 | 89 | 49 | 15 |
| 3-Analog | 100 | 100 | 100 | 39 | −1 | — |

*Doses are in µg/ml.

These data demonstrate a marked improvement in activity that is at least a 5-fold increase in the leukotriene inhibitor assay.

What is claimed is:

1. A compound of the formula:

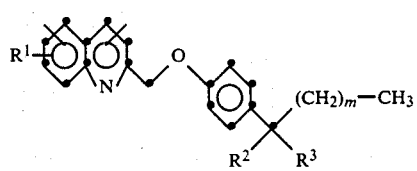

wherein:

$R^1$ is H, halogen, $C_1$-$C_6$ alkyl, —$CF_3$, —$OR^2$, —$SR^2$, —CHO, —$COOR^2$, —(C=O)$R^2$, —C(OH)$R^2R^2$, —CN, —$NO_2$, unsubstituted phenyl, unsubstituted benzyl, or unsubstituted phenethyl;

$R^2$ is H or $C_1$-$C_6$ alkyl, $R^3$ is —$OR^4$, —$SR^4$, or —$NR^4R^4$;

$R^4$ is H, or $C_1$-$C_6$ alkyl, —(C=O)$R^2$, unsubstituted phenyl, or unsubstituted benzyl;

m is 1-6; and the pharmaceutically acceptable salts thereof.

2. A compound of claim 1 wherein $R^2$ is H, $R^3$ or OH, and m is 4.

3. The compound of claim 1: 2-[4-(1-hydroxyhexyl)-phenoxymethyl)] quinoline.

4. A pharmaceutical composition useful in antagonizing leukotriene action in mammals comprising an amount of a compound of claim 1 effective as a leukotriene antagonist and a pharmaceutically acceptable carrier 5. A pharmaceutical composition of claim 4 useful in antagonizing leukotriene $D_4$ action in mammals.

6. A method of preventing the synthesis, the action, or the release of SRS-A and leukotriene $D_4$, in mammals, which comprises administering to said mammal an effective amount of a compound of claim 1.

7. The method of claim 6 wherein leukotriene $D_4$ is affected.

* * * * *